United States Patent
Hagay et al.

(10) Patent No.: US 10,538,737 B2
(45) Date of Patent: Jan. 21, 2020

(54) POMEGRANATE DERIVED CELL CULTURE AND METHODS FOR PREPARING AND USING THE SAME

(71) Applicant: BIO HARVEST LTD., Rehovot (IL)

(72) Inventors: Yoheved Hagay, Rehovot (IL); Malkit Azachi, Rehovot (IL); Rivka Yatuv, Shoham (IL)

(73) Assignee: BIO HARVEST LTD., Rehovot (IL)

( * ) Notice: Subject to any disclaimer, the term of this patent is extended or adjusted under 35 U.S.C. 154(b) by 74 days.

(21) Appl. No.: 15/109,649

(22) PCT Filed: Jan. 5, 2015

(86) PCT No.: PCT/IL2015/050018
§ 371 (c)(1),
(2) Date: Jul. 4, 2016

(87) PCT Pub. No.: WO2015/102003
PCT Pub. Date: Jul. 9, 2015

(65) Prior Publication Data
US 2016/0348068 A1    Dec. 1, 2016

Related U.S. Application Data

(60) Provisional application No. 61/923,688, filed on Jan. 5, 2014.

(51) Int. Cl.
*C12N 5/04* (2006.01)
*A61K 36/18* (2006.01)
*A61K 36/185* (2006.01)

(52) U.S. Cl.
CPC ............ *C12N 5/04* (2013.01); *A61K 36/185* (2013.01); *C12N 2500/34* (2013.01); *C12N 2511/00* (2013.01)

(58) Field of Classification Search
None
See application file for complete search history.

(56) References Cited

U.S. PATENT DOCUMENTS

| 6,069,009 A | 5/2000 | Pepin et al. |
| 2003/0005489 A1 | 1/2003 | Gray et al. |
| 2010/0112700 A1* | 5/2010 | Shaaltiel ................ C12M 23/26 435/410 |
| 2012/0328593 A1 | 12/2012 | Huang et al. |

FOREIGN PATENT DOCUMENTS

| CN | 101619326 | 1/2010 |
| CN | 101619326 B * | 7/2011 |
| WO | WO2006/090388 | 8/2006 |
| WO | WO-2006090388 A2 * | 8/2006 ............ A01H 4/005 |

OTHER PUBLICATIONS

Naik et al 2011 (Plant Cell Reports 30: p. 707-721).*
Yesil-Celiktas et al 2010 (Large Scale Cultivation of Plant Cell and Tissue Culture in Bioreactors p. 1-54).*
Mulabagal et al 2004 (International Journal of Applied Science and Engineering 2:1 p. 29-48).*
Ducos et al. Improvement of plastic-based disposable bioreactors for plant science needs. Phytochemistry Reviews, Oct. 2008. vol. 7. No. 3 pp. 607-613 Abstract; pp. 612, col. 1, para1.
International Search Report for PCT application No. PCT/IL2015/050018 dated May 18, 2015.

* cited by examiner

*Primary Examiner* — Matthew R Keogh
(74) *Attorney, Agent, or Firm* — The Roy Gross Law Firm, LLC; Roy Gross

(57) ABSTRACT

The invention relates to a large scale process for the in vitro production of a cell culture of pomegranate cells, to a product prepared from such cells and to a composition comprising a complex of pholyphenols, including punicalagin, 1,2,3,4,6-pentagalloyl glucose (PGG) or both.

13 Claims, No Drawings

POMEGRANATE DERIVED CELL CULTURE AND METHODS FOR PREPARING AND USING THE SAME

CROSS-REFERENCE TO RELATED APPLICATIONS

This application is a National Phase Application of PCT International Application No. PCT/IL2015/050018, International Filing Date Jan. 5, 2015, claiming the benefit of U.S. Provisional Patent Application No. 61/923,688, filed Jan. 5, 2014, all of which are hereby incorporated by reference.

FIELD OF THE INVENTION

This invention is directed to pomegranate derived cell culture, a process for the large scale production of such cells, as well as methods of using the same.

BACKGROUND OF THE INVENTION

Large scale processes are known in the art and are necessary for the industrial production of various materials. Since large scale processes cannot be performed by the same means as small scale processes, specific processes for the large scale production of materials must be designed, even if small scale processes exist.

Nutraceuticals are sometimes prepared using synthetic processes that provide the desired active ingredients, e.g., polyphenols, which are naturally found in fruit cells. However, the use of synthetic processes does not provide the natural ingredients along with the active ingredients, which sometimes contribute to the efficiency of the formulation.

Other types of nutraceuticals are prepared from the natural plants; however, all known large scale processes for preparing nutraceuticals from plants include the extraction of the prepared plant cells in order to obtain the desired active ingredient. However, when plants containing polyphenols, for example, are extracted, the final product may be hitter. Also, only certain parts of the plant may be successfully extracted since only they contain the desired amounts of the active ingredients.

Small scale processes for the preparation of fruit cells are known in the art; however, large scale processes are more difficult to design since they tend to amplify the production of the primary metabolites, while minimizing the productions of the secondary metabolites. Since active ingredients, such as polyphenols, are secondary metabolites their production in large-scale processes is complex.

Nutraceuticals derived from polyphenol-containing fruit extracts are known for their beneficial effects. However, it has been shown that the therapeutic effect of fruit extracts is dependent on species, location, year (annual climate), processing etc. and therefore reliance on natural fruits as a source of these regulatory compounds does not lead to a homogeneous or consistent supply of material. Furthermore, fruits are often contaminated by residual fungicides, pathogens, pesticides and pollutants.

Nonetheless, dietary consumption of polyphenols was shown to be inversely related to morbidity and mortality from coronary heart disease (CHD). Moreover, an inverse association between polyphenols intake and subsequent occurrence of ischemic heart disease, or cerebrovascular disease was shown. Over the last decade, studies indicated that pomegranate is a potent antioxidant and its therapeutic properties further include treatment and prevention of cardiovascular disease, erectile dysfunction, dental conditions and protection from ultraviolet radiation. Other potential applications include infant brain ischemia, Alzheimer's disease, arthritis and obesity.

Thus, there is a need in the art for a large scale process for preparing fruit cells from natural ingredients, which includes the production of both the primary and the secondary metabolites of the fruit cells. There is need for natural (phyto) compositions that may be prepared in a large scale process in which the amount of the active ingredient is consistent and recurrent (e.g., clonal preparations), is highly bioavailable and easily administered for the treatment and prevention of various diseases and disorders.

Pomegranate juice and fruit extracts (including seeds, inner lamellae, mesocarp and exocarp), as well as plant parts, such as, bark, roots, and leaves, exhibit potent biological properties attributable to the presence of polyphenols. Polyphenols content of pomegranate includes flavonoids, phenolic acids and tannins, all of which are present in various plant parts, such as, bark, leaf and fruit seeds, inner lamellae, mesocarp and exocarp. Within the fruit, juice polyphenols include mainly anthocyanins such as cyanidin-3-glycoside, cyanidin-3,3-diglycoside, and delphindin-3-glucoside) and anthoxanthins (such as catechins, ellagic tannins, and gallic and ellagic acids, whereas hydrolysable ellagitannins are found mostly in the peels.

Ellagic acid and hydrolysable ellagitannins are both implicated in protection against atherogenesis, along with their potent antioxidant capacity. Punicalagin is the major ellagitannin in pomegranate, and this compound is responsible for the high antioxidant activity of this juice. An additional polyphenol found in pomegranate (mainly in the leaves) is 1,2,3,4,6-pentagalloyl glucose (PGG). PGG is a component of plants traditionally used in Chinese medicine, as well as in other fruits such as mango and banana. PGG has recently been shown to prevent biofilm formation by *S. aureus* and bind insulin receptor and thus to activate insulin-mediated glucose transport signaling pathway and to induce p53 and apoptosis in cancer cells through insulin receptor signaling.

Due to the extensive knowledge about the pomegranate's health attributes and increasing public awareness about functional food, the demand for pomegranate fruit and its byproduct has increased tremendously in the western world. As a result of this trend, the extent of pomegranate growth was increased significantly in many regions throughout the world, and industries that produced pomegranate products have been developed.

Pomegranate-derived callus cultures have been generated by several research groups. However, the cultures developed so far have been used for in vitro organogenesis and plant regeneration and the expression of secondary metabolites as an ingredient in nutraceutical products was not tested Therefore, there is a need in the for the production of a pomegranate cell culture-based product that includes both the primary and the secondary metabolites of the pomegranate cells.

SUMMARY OF THE INVENTION

In an embodiment of the invention, there is provided a large scale process for the in vitro production of a pomegranate cell culture of pomegranate cells grown comprising: growing pomegranate cells in a flask;
inoculating the pomegranate cells from the flask into a first bioreactor;
inoculating the pomegranate cells from the first bioreactor into a second bioreactor; and harvesting the pomegranate cells from the last bioreactor; wherein the second bioreactor is a last bioreactor or an intermediate bioreactor and wherein at least one of the first and the second bioreactor is disposable and wherein the pomegranate cells harvested from the last bioreactor are dried.

In some embodiments, the invention provides a composition in a form of a powder comprising pomegranate fruit cells grown in vitro, whereby the pomegranate cells are derived from one or more of section: pomegranate skin, pomegranate lamellae and/or pomegranate seeds.

In further embodiments, the invention provides a method of treating inflammation comprising administering an effective amount of a composition comprising composition in a form of a powder comprising pomegranate fruit cells grown in vitro, whereby the pomegranate cells are derived from one or more of cross section, pomegranate skin, pomegranate lamellae and/or pomegranate seeds.

In some embodiments of the invention, there is provided a pomegranate callus derived from one or more of pomegranate skin, pomegranate lamellae or pomegranate seeds, wherein the pomegranate callus contains a complex of pholyphenols, and one or more of PGG or puniclagin.

The pomegranate callus of the present invention that comprises punicalagin or 1,2,3,4,6-pentagalloyl glucose (PGG) or both was not described before.

Further, the pomegranate cell culture that is grown in vitro, as well as the products of the large scale process as described herein (the product of the pomegranate cell growth in Erlenmeyer or in the various bioreactors as described in the examples section also contains punicalagin or 1,2,3,4,6-pentagalloyl glucose (PGG) or both.

In some embodiments of the invention, there is provided a composition in a form of a powder comprising pomegranate fruit cells grown in vitro, whereby the pomegranate cells are derived from one or more of pomegranate skin, pomegranate lamellae and/or pomegranate seeds. The pomegranate fruit cells grown in vitro include punicalagin or 1,2,3,4,6-pentagalloyl glucose (PGG) or both. In some embodiments, the pomegranate cell culture that contains punicalagin or 1,2,3,4,6-pentagalloyl glucose (PGG) or both is grown in vitro in a large scale process.

DETAILED EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the invention are directed to a composition in a form of a powder comprising a cell culture of pomegranate cell culture (PC) grown in vitro in, whereby the cell culture of PC is derived from one or more of pomegranate sections: pomegranate skin exocarp, mesocarp, pomegranate lamellae and pomegranate seeds. In an embodiment of the invention, the cell culture of PC includes punicalagin and PGG in an amount of at least 1300 mg punicalagin/kg powder and 2600 mg PGG/kg powder.

According to some embodiments, there is provided a process for the large scale in vitro production of pomegranate cell cultures. In some embodiments of the invention, the process does not include the extraction of the fruit cells. Surprisingly, the produced fruit cell cultures, manufactured in accordance with the large scale process described herein, were shown to include high amount of polyphenols particularly, the secondary metabolites punicalagin and PGG. The unique composition of pomegranate cells (PC), which as an outcome of scale up process, includes of a whole matrix of polyphenols and other healthy ingredients, naturally existing in PC, with higher concentration of pomegranate punicalagin and PGG than the concentration that is found in fresh pomegranates.

As used herein the term "polyphenols" refers to naturally occurring phyto organic compounds having more than one phenol group. Polyphenols may range from simple molecules, such as phenolic acid, to large, highly polymerized, compounds such as hydrolyzed tannins. The phenolic rings of polyphenols are typically conjugated to various sugar molecules, organic acids and/or lipids. Differences in this conjugated chemical structure account for the chemical classification and variation in the modes of action and health properties of the various polyphenol compounds. Examples of polyphenols include, but are not limited to, anthocyanins, proanthocyanins and hydrolyzable tannins. Typical pomegranate polyphenols include but not limited to ellagitannins (e.g. punicalagin and punicalin), gallic and ellagic acids and 1,2,3,4,6-pentagalloyl glucose (PGG). The pomegranate fruit may be of a wild or cultivated variety.

According to some embodiments, the calli cells and/or suspension culture of pomegranate cells is derived from one or more of pomegranate fruit cross sections: pomegranate skin; exocarp, mesocarp, pomegranate lamellae and/or pomegranate seeds.

Some embodiments are directed to a composition comprising non-extracted, dry calli cells culture of pomegranate fruit cells. According to some embodiments, the calli cells culture is grown in vitro. According to some embodiments, the cell culture comprises both primary and secondary metabolites.

Some embodiments are directed to a method for the production of polyphenols from a culture of pomegranate cells. According to some embodiments of the invention, although the amount of materials, including polyphenols, may vary in different batches of fruit, the use of a culturing protocol for preparing the fruit cell cultures ensures the reproducibility of the preparation and its contents. Thus, various batches of fruit cells, prepared from the same culture have a typical HPLC fingerprint. According to some embodiments, the concentrations of the various materials in each batch may change, though, as mentioned above, if prepared from the same culture, the HPLC fingerprint is consistent for all batches.

According to some embodiments, the relative amounts of the various polyphenols in the prepared pomegranate fruit cells, differ from the relative amounts thereof in the agricultural pomegranate fruit as shown in table 5. According to some embodiments, the amount of certain polyphenols is amplified in the prepared fruit cells, in comparison to their amount in the agricultural pomegranate fruit.

According to some embodiments, the amount of punicalagin and PGG in the pomegranate cell cultures, is between 1000-100000 mg/kg after the pomegranate cell cultures are dried to a powder. According to some embodiments of the invention, the amount is more than 1000 mg/kg after the pomegranate cell cultures are dried to a powder. According to some embodiments of the invention, the amount is more than 3000 mg/kg after the pomegranate cell cultures are dried to a powder. According to some embodiments, the amount is more than 5000 mg/kg after the pomegranate cell cultures are dried to a powder. According to some embodiments of the invention, the amount is more than 10000 mg/kg after the pomegranate cell cultures are dried to a powder. According to some embodiments of the invention, the amount is more than 20000 mg/kg after the pomegranate cell cultures are dried to a powder. According to some embodiments of the invention, the amount is more than 30000 mg/kg after the pomegranate cell cultures are dried to a powder. According to some embodiments of the invention, the amount is more than 40000 mg/kg after the pomegranate cell cultures are dried to a powder. According to some embodiments of the invention, the amount is more than 50000 mg/kg after the pomegranate cell cultures are dried to a powder. According to some embodiments of the invention, the amount is more than 60000 mg/kg after the pomegranate cell cultures are dried to a powder. According to some embodiments of the invention, the amount is more than 70000 mg/kg after the pomegranate cell cultures are dried to a powder.

According to some embodiments, the relative amounts of various ingredients in the prepared pomegranate cell cultures, differ from the relative amounts thereof in the agricultural pomegranate fruit. According to some embodiments, the relative amount of sugar in the pomegranate cell cultures is reduced in comparison to the relative amount of the sugar in the agricultural pomegranate fruit.

According to some embodiments, the pomegranate cell cultures prepared according to the large scale method of the invention contain less than 10% w/v sweetening sugar. According to some embodiments, the pomegranate cell cultures contain less than 5% w/v sweetening sugar. According to some embodiments, the pomegranate cell cultures contain less than 3% w/v sweetening sugar. According to some embodiments, the pomegranate cell cultures contain less than 2% w/v sweetening sugar. According to some embodiments, the pomegranate cell cultures contain less than 1% w/v sweetening sugar. According to some embodiments, the pomegranate cell cultures contain about 1% w/v sweetening sugar. As used herein, the phrase "a sweetening sugar" refers to a sugar which provides a sweet taste e.g. sucrose, glucose and fructose.

According to some embodiments, the pomegranate cell cultures are dried, thus concentrating the materials found therein, including the sugar. According to some embodiments, the materials are concentrated by a factor of 5. According to some embodiments, the materials are concentrated by a factor of 10. According to some embodiments, the materials are concentrated by a factor of 15. According to some embodiments, the materials are concentrated by a factor of 20. According to some embodiments, the materials are concentrated by a factor of 25. According to some embodiments, the materials are concentrated by a factor of 30.

According to one embodiment, the dried pomegranate cell cultures contains up to 10% w/v sweetening sugar. According to some embodiments of the invention, the dried pomegranate cell cultures contains up to 15% w/v sweetening sugar. According to one embodiment, the dried pomegranate cell cultures contain between 10-15% w/v sweetening sugar. According to one embodiment, the dried pomegranate cell cultures contain between 15-20% w/v sweetening sugar. According to one embodiment, the dried pomegranate cell cultures contain less than 20% w/v sweetening sugar. According to one embodiment, the dried pomegranate cell cultures contain less than 30% w/v sweetening sugar.

According to some embodiments, the pomegranate cell cultures prepared according to the large scale method of the invention are tasteless. According to other embodiments, the pomegranate cell cultures prepared according to the large scale method of the invention are tasteful.

In some embodiments of the invention, there is provided a pomegranate callus derived from one or more of pomegranate skin, pomegranate lamellae or pomegranate seeds, wherein the pomegranate callus contains a complex of pholyphenols, and one or more of PGG or puniclagin.

The pomegranate callus of the present invention that comprises punicalagin or 1,2,3,4,6-pentagalloyl glucose (PGG) or both was not described before. Further, the pomegranate cell culture that is grown in vitro, as well as the products of the large scale process described herein (the product of the growth in Erlenmeyer or in the various bioreactors described in the examples section, contains punicalagin or 1,2,3,4,6-pentagalloyl glucose (PGG) or both.

In some embodiments of the invention, there is provided a composition in a form of a powder comprising pomegranate fruit cells grown in vitro, whereby the pomegranate cells are derived from one or more of pomegranate skin, pomegranate lamellae and/or pomegranate seeds. The pomegranate fruit cells grown in vitro include punicalagin or 1,2,3,4,6-pentagalloyl glucose (PGG) or both. In some embodiments, the pomegranate cell culture is grown in vitro in a large scale process.

By the term "a complex of pholyphenols" it is meant including flavonoids, phenolic acids and tannins with a similar composition to the complex of polyphenols found in the pomegranate fruit.

By the term total polyphenols it is mean the complex of polyphenols including the PGG and/or the punicalagin.

According to some embodiments, the amount of each the PGG or punicalagin in the pomegranate callus is between about 0.1-10% (w/w). This amount is equivalent to 1000-100,000 mg/kg of dry weight of callus.

According to some embodiments of the invention, the amount of each the PGG or the punicalagin is between about 0.2-10% (w/w).

According to some embodiments of the invention, the amount of each the PGG or the punicalagin is between about 0.5-8% (w/w).

According to some embodiments of the invention, the amount of each the PGG or the punicalagin is between about 1-7% (w/w).

According to some embodiments of the invention, the amount of each the PGG or the punicalagin is between about 2-8% (w/w).

According to some embodiments of the invention, the amount of each the PGG, punicalagin in the pomegranate composition in a form of a powder comprising pomegranate fruit cells grown in vitro, whereby the pomegranate cells are derived from one or more of pomegranate skin, pomegranate lamellae and/or pomegranate seeds is between about 0.1-10% (w/w). This amount is equivalent to 1000-100,000 mg/kg of dry weight of powder.

According to some embodiments of the invention, the amount of each the PGG or the punicalagin is between about 0.1-8% (w/w).

According to some embodiments of the invention, the amount of each the PGG or the punicalagin is between about 0.1-6% (w/w).

According to some embodiments of the invention, the amount of each the PGG or the punicalagin phenols is between about 0.1-5% (w/w).

According to some embodiments of the invention, the amount of each the PGG or the punicalagin is between about 0.1-4% (w/w).

According to some embodiments, the amount of each of the punicalagin and the PGG in the callus is at about 0.1, 0.2, 0.3, 0.4, 0.5, 0.6, 0.7, 0.8, 0.9, 1% w/w or more.

According to some embodiments, the amount of each the punicalagin and the PGG in the callus is between about 0 to 1.5% w/w. The total amount of the polyphenols is between about 0.1-80%, 0.1-70%, 0.1-35%, 0.1-30% w/w.

According to some embodiments, the amount of each of the punicalagin and the PGG in the cell culture after being grown in an Erlenmeyer is between about 0.1, 0.2, 0.3, 0.4, 0.5, 0.6, 0.7, 0.8, 0.9, 1% w/w or more. The total amount of the polyphenols is between about 0.1, 0.5, 1, 1.5, 2, 2.5, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 w/w or more.

According to some embodiments of the invention, the amount of punicalagin and the PGG in the cell culture after being grown in an Erlenmeyer and transferred to bioreactors according to the embodiments of the invention is between about 0.5 to 3% w/w. The total amount of the polyphenols is between about 0.5-80%, 1-80%, 3-80%, 7-75%, 6-75%, 10-70% w/w.

According to some embodiments of the invention, the amount of each of the punicalagin and the PGG in the cell culture after being grown in an Erlenmeyer and transferred to bioreactors according to the embodiments of the invention is about 0.2, 0.3, 0.4, 0.5, 0.6, 0.7, 0.8, 0.9, 1% w/w or more. The total amount of the polyphenols is about 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 70%, 80% w/w or more.

In one embodiment of the invention, there is provided a process for the in vitro production of a cell culture of pomegranate fruit cells grown comprising: growing pomegranate cells in a flask;
inoculating the pomegranate cells from the flask into a first bioreactor; and harvesting the produced pomegranate cells.

In some embodiments of the invention, there is provided a large scale process for the in vitro production of a cell culture of pomegranate fruit cells grown comprising:
growing pomegranate cells in a flask;
inoculating the pomegranate cells from the flask into a first bioreactor; inoculating the pomegranate cells from the first bioreactor into a second bioreactor, wherein the second bioreactor is a last bioreactor or an intermediate bioreactor and there may be provided some more steps with one or more intermediate bioreactors and wherein at least one of the first and the second bioreactor is disposable; and
harvesting the pomegranate cells from the last bioreactor; wherein the pomegranate cells harvested from the last bioreactor are dried.

By a "disposable bioreactor" it is meant a bioreactor with a disposable bag, which can be for a single use bag instead of a culture vessel. The disposable bag is typically made of three layers or more plastic foil. In some embodiments of the invention, one layer is made from polyethylene, polyethylene terephthalate or LDPE to provide mechanical stability. A second layer is made using nylon, PVA or PVC that acts as a gas barrier. Finally, a contact layer is made from PVA or PP or another layer of polythyelene, polyethylene terephthalate or LDPE. For medical applications the single-use materials that contact the product must be certified by the European Medicines Agency or similar authorities responsible for other regions.

According to some embodiments of the invention, the disposable bioreactor is made from one or more layers of polyethylene. In some embodiments of the invention, the disposable bioreactor is made from an inner and outer layer of polyethylene and a middle nylon layer.

In general there are two different approaches for constructing single-use bioreactors, differing in the means used to agitate the culture medium.

Some single-use bioreactors use stirrers like conventional bioreactors, but with stirrers that are integrated into the plastic bag. The closed bag and the stirrer are pre-sterilized. In use the bag is mounted in the bioreactor and the stirrer is connected to a driver mechanically or magnetically.

Other single-use bioreactors are agitated by a rocking motion. Other single-use bioreactors are airlift bioreactor in which the reaction medium is agitated and aerated by introduction of air. This type of bioreactor does not need any mechanical agitators inside the single-use bag.

According to some embodiments, the large scale process for preparing pomegranate cell cultures is comprised of a number of subsequent steps. According to some embodiments of the invention, the amount of pomegranate cell cultures prepared in each step is either larger or not than that prepared in the previous step. Further, the pomegranate cell cultures prepared in each step may be inoculated or harvested to be used as a starter for the next step of the large scale process. In the last step of the large scale process, the fruit cells are typically grown until they reach the plateau in their growth profile.

According to some embodiments, there is provided a composition comprising a complex of pholyphenols including punicalagin and PGG (1,2,3,4,6-pentagalloyl glucose), wherein the amount of the punicalagin and PGG to polyphenols is higher than 1:20. In some embodiments, the ratio is higher than 1:10. In some embodiments, the ratio is higher than 1:5. In some embodiments, the ratio is higher than. In some embodiments, the ratio is higher than 1:3. In some embodiments, the ratio is higher than 1:2.

According to some embodiments, the composition is derived from a natural source. According to some embodiments, the composition is derived from pomegranate cell cultures grown in large scale disposable bioreactors. According to some embodiments, the composition is derived from pomegranate cell cultures grown in large scale disposable bioreactors according to the process described herein.

According to some embodiments, the pomegranate cells are grown in bioreactors. According to some embodiments, the bioreactors are designed so as to allow adequate mixing and mass transfer, while minimizing the intensity of shear stress and hydrodynamic pressure. According to some embodiments of the invention, at least one of the bioreactors is a disposable bioreactor. This can be the first bioreactor or the intermediate bioreactor or the last bioreactor or any combination thereof. According to some embodiments of the invention, the disposable bioreactor is the last bioreactor after which the cells are harvested and dried so as to form a powder.

According to an exemplary embodiment of the invention, the first step includes the preparation of a pomegranate cell culture in a flask, such as an Erlenmeyer or a bioreactor. According to some embodiments, the first step involves the preparation of up to 1.0 L of a pomegranate cell culture. According to further embodiments, first step involves the preparation of up to 1.5 L of a pomegranate cell culture. According to further embodiments, first step involves the preparation of up to 2.0 L of a pomegranate cell culture.

According to some embodiments, the first step is conducted using a glass, metal or plastic flask. According to some embodiments, the flask is disposable. According to further embodiments, the flask may be reused any number of times. According to some embodiments, the flask is sterilized by any appropriate means between uses.

According to some embodiments, the first step includes the use of any appropriate medium for growing the pomegranate cells. According to some embodiments, the medium used for growing the fruit cells includes cell growth medium, salts, vitamins, sugars, hormones or any combination thereof. According to some embodiments, the cell growth medium includes B5 Gamborg (Gamborg et al., Exp. Cell Res. 50:151, 1968), or any modification thereof.

According to some embodiments, the cell growth medium includes liquid M-6 medium (Murashige and Skoog medium; Murashige et al., Physiol Plant 15(3): 473-497, 1962), or any modification thereof. According to further embodiments, the cell growth medium includes either liquid M-6 medium or Gamborg B5 medium. According to some embodiments, the cell growth medium is Gamborg B5 medium supplemented with sucrose, casein hydrolysate, myoinositol, 1-naphthaleneacetic acid (NAA) and kinetin, or any combination thereof. The medium is designated as E-med.

According to some embodiments, the growth medium, designated as E-med, is supplemented with about 1-4% sucrose, about 0.2-0.3 g/L casein hydrolysate, about 0.05-0.15 g/L myo inositol, about 0.05-0.15 mg/L NAA and about 0.1-0.3 mg/L kinetin the medium pH 5.4-5.45.

As can be seen from the Examples and from Table 5, the use of E-med growth medium resulted in pomegranate cell culture grown in a suspension that has the highest amount of total polyphenols, punicalagin and PGG.

According to some embodiments, the growth medium comprises salts such as magnesium, phosphate, nitrate or any combination thereof. According to some embodiments of the invention, the growth medium includes $KNO_3$, $MgSO_4$, $NaH_2PO_4$, or any combination thereof. According to some embodiments, the medium includes Gamborg B5, vitamins or any combination thereof. According to further embodiments, the medium includes sugars such as sucrose, Gamborg B5 or any combination thereof.

In an embodiment of the invention, the concentration of the $KNO_3$ added to the growth medium is between 25 mM to 45 mM.

In an embodiment of the invention, the concentration of the $MgSO_4$ added to the growth medium is between 1 mM to 15 mM.

In an embodiment of the invention, the concentration of the $MgNO_3$ added to the growth medium is between 5 mM to 35 mM.

In an embodiment of the invention, the concentration of the $KNO_3$ added to the growth medium is between 15 mM to 60 mM.

In an embodiment of the invention, the concentration of the $MgSO_4$ added to the growth medium is between 0.5 mM to 25 mM.

In an embodiment of the invention, the concentration of the $MgNO_3$ added to the growth medium is between 1 mM to 50 mM.

In an embodiment of the invention, the concentration of the $KNO_3$ added to the growth medium is between 30 mM to 40 mM.

In an embodiment of the invention, the concentration of the $MgSO_4$ added to the growth medium is between 5 mM to 10 mM.

In an embodiment of the invention, the concentration of the $MgNO_3$ added to the growth medium is between 20 mM to 30 mM.

In an embodiment of the invention, myo-inositol is added to the growth medium.

In an embodiment of the invention, $H_3BO_3$ is added to the growth medium.

In an embodiment of the invention, $MnSO_4$ is added to the growth medium.

In an embodiment of the invention, $NaH_2PO_4$ is added to the growth medium.

In an embodiment of the invention, Biotin is added to the growth medium.

In an embodiment of the invention, D-Pantothenate calcium is added to the growth medium.

In an embodiment of the invention, about 0.5 mM myo-inositol is added to the growth medium.

In an embodiment of the invention, about 0.05 mM $H_3BO_3$ is added to the growth medium.

In an embodiment of the invention, about 0.04 mM $MnSO_4$ is added to the growth medium.

In an embodiment of the invention, about 1 mM $NaH2PO_4$ is added to the growth medium.

In an embodiment of the invention, about 0.004 mM Biotin is added to the growth medium.

In an embodiment of the invention, about 0.2 mM D-Pantothenate calcium is added to the growth medium.

In an embodiment of the invention, about 0.1, 0.2, 0.3, 0.4, 0.5, 0.6, 0.7, 0.8, 0.9, 1.0, 2, 3, 4, 5, 6, 7, 8, 9, 10 mM myo-inositol is added to the growth medium.

In an embodiment of the invention, about 0.01, 0.02, 0.03, 0.04, 0.05, 0.06, 0.07, 0.08, 0.09, 0.1 mM $H_3BO_3$ is added to the growth medium.

In an embodiment of the invention, about 0.01, 0.02, 0.03, 0.04, 0.05, 0.06, 0.07, 0.08, 0.09, 0.1 mM $MnSO_4$ is added to the growth medium.

In an embodiment of the invention, 0.1, 0.2, 0.3, 0.4, 0.5, 0.6, 0.7, 0.8, 0.9, 1.0, 2, 3, 4, 5, 6, 7, 8, 9, 10 mM $NaH_2PO_4$ is added to the growth medium.

In an embodiment of the invention, about 0.001, 0.002, 0.003, 0.004, 0.005, 0.006, 0.007, 0.008, 0.009, 0.01 mM Biotin is added to the growth medium.

In an embodiment of the invention, about 0.1, 0.2, 0.3, 0.4, 0.5, 0.6, 0.7, 0.8, 0.9, 1.0, 2, 3, 4 mM D-Pantothenate calcium is added to the growth medium.

In an embodiment of the invention, the concentration of the sucrose added to the growth medium is between 2 to 4%. In another embodiment, the concentration is about 3%.

According to further embodiments, casein, casein hydrolysate or casein peptone may be included in the cell growth medium. According to further embodiments growth hormones may be included in the cell growth medium. According to further embodiments, the growth medium includes hormones. According to some embodiments the pomegrante cells are grown without the addition of hormones.

Examples of plant culture media that may be used according to some embodiments in one stage or more of the process, include, but are not limited to: Anderson (Anderson, In Vitro 14:334, 1978; Anderson, Act. Hort., 112:13, 1980), Chee and Pool (Sci. Hort. 32:85, 1987), CLC/Ipomoea (CP) (Chee et al., J. Am. Soc. Hort. Sci. 117:663, 1992), Chu (N.sub.6) (Chu et al., Scientia Sinic. 18:659, 1975; Chu, Proc. Symp. Plant Tiss. Cult., Peking 43, 1978), DCR (Gupta and Durzan, Plant Cell Rep. 4:177, 1985), DKW/Juglans (Driver and Kuniyuki, HortScience 19:507, 1984; McGranahan et al., in: Bonga and Durzan, eds., Cell and Tissue Culture in Forestry, Martinus Nijhoff, Dordrecht, 1987), De Greef and Jacobs (De Greef and Jacobs, Plant Sci. Lett. 17:55, 1979), Eriksson (ER) (Eriksson, Physiol. Plant. 18:976, 1965), Gresshoff and Doy (DBM2) (Gresshoff and Doy, Z Pflanzenphysiol. 73:132, 1974), Heller's (Heller, Ann. Sci. Nat. Bot. Biol. Veg. 11th Ser. 14:1, 1953), Hoagland's (Hoagland and Arnon, Circular 347, Calif. Agr. Exp. Stat, Berkeley, 1950), Kao and Michayluk (Kao and Michayluk, Planta 126:105, 1975), Linsmaier and Skoog (Linsmaier and Skoog, Physiol. Plant. 18:100, 1965), Litvay's (LM) (Litvay et al., Plant Cell Rep. 4:325, 1985), Nitsch and Nitsch (Nitsch and Nitsch, Science 163:85, 1969), Quoirin and Lepoivre (Quoirin et al., C. R. Res. Sta. Cult. Fruit Mar., Gembloux 93, 1977), Schenk and Hildebrandt (Schenk and Hildebrandt, Can. J. Bot. 50:199, 1972), White's (White, The Cultivation of Animal and Plant Cells, Ronald Press, N Y, 1963), etc.

According to some other exemplary embodiments, the pomegranate cells and the medium are continuously mixed during the first step. According to further embodiments, the pomegranate cells and the medium are mixed occasionally during the first step. According to some embodiments, the temperature during the first step is between 20° C. and 30° C. According to some embodiments, the temperature during the first step is between 22° C. and 28° C. According to some embodiments, the pomegranate cells are grown in the first step for more than 5 days. According to some embodiments, the pomegranate cells are grown in the first step for more than 7 days. According to some embodiments, the pomegranate cells are grown in the first step for more than 5 days and less than 3 weeks. According to some embodiments, the pomegranate cells are grown in the first step for more than 5 days and less than 21 days.

According to some exemplary embodiments, the bioreactor used in the process of the invention includes an inlet through which the pomegranate cells from the first step, the medium and any additional materials are placed into the bioreactor. According to further embodiments, the bioreactor used in the process of the invention includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the flask once the atmosphere in the flask reaches a pre-defined pressure. According to some embodiments, the predefined pressure up to 8 PSI.

Once the first step of the pomegranate cell growth is concluded, according to some exemplary embodiments, the pomegranate cells are inoculated into a small scale bioreactor, which is termed here also the first bioreactor. For the second step of the large scale process. According to some embodiments, the small scale bioreactor is a 4 L reactor. According to further embodiments, the small scale bioreactor is a 3-5 L reactor. According to further embodiments, the small scale bioreactor is a 3-10 L reactor. According to further embodiments, the small scale bioreactor is a 4-8 L reactor.

The small scale bioreactor may be prepared from any appropriate material, such as glass, metal, plastic and/or any type of polymer. According to some embodiments, the small scale bioreactor is disposable. If the small scale bioreactor is not disposable, according to some embodiments, it is cleaned and sterilized between uses by any appropriate means.

As described above, the production of secondary metabolites, including polyphenols, is known to be significantly reduced with increasing bioreactors volumes, in comparison to the amount of the same metabolites in small scale productions, using, e.g., glass flasks, such as Erlenmeyers. However, the large scale process detailed herein provides pomegranate cells in which the amount of the secondary metabolites is not reduced when grown in bioreactors. Further, the production of certain secondary metabolites may even be amplified.

Thus, according to embodiments of the invention, the relative amounts of the secondary metabolites in pomegranate cells grown in the small scale bioreactor are not significantly reduced in comparison to their relative amounts in the first step of the process. According to some embodiments, the components described above for use in the growth medium in the first step may be used also in the second step of the process. According to some embodiments, the growth medium used in the small scale bioreactor is the same as used in the first step of the large scale process. According to some embodiments, the relative amounts of the different components found in the growth medium in the second step, is the same as in the first step. According to other embodiments, the relative amounts of the different components found in the growth medium in the second step, differ from the relative amounts used in the first step. According to some embodiments, additional materials are added to the growth medium in the second step of the process.

According to some embodiments, the small scale bioreactor includes an inlet through which the fruit cells from the first step, air, the medium and any additional materials are placed into the bioreactor. According to further embodiments, the small scale bioreactor includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the bioreactor once the atmosphere in the bioreactor reaches a pre-defined pressure. According to some embodiments, the predefined pressure is 8 PSI.

According to some embodiments, the pomegranate cells and the medium are continuously mixed during the second step. According to further embodiments, the pomegranate cells and the medium are mixed occasionally during the second step. According to some embodiments, the temperature during the second step is between 20 to 30° C. According to some embodiments, the pomegranate cells are grown in the second step for more than a week and less than two weeks. In some embodiments of the invention, the pomegranate cells are grown between 10-30 days before being inoculated into the next bioreactor.

For the third step of the large scale process, the harvested pomegranate cells are placed into a large scale bioreactor. According to some embodiments, the large scale bioreactor is a 30-50 L reactor. According to further embodiments, the large scale bioreactor is a 40-60 L reactor. According to further embodiments, the large scale bioreactor is a 30-70 L reactor. According to further embodiments, the large scale bioreactor is a 20-100 L reactor.

The large scale bioreactor may be prepared from any appropriate material, such as glass, metal, plastic and/or any type of polymer. According to some embodiments, the large bioreactor is disposable. If the large scale bioreactor is not disposable, according to some embodiments, it is cleaned and sterilized between uses by any appropriate means.

Similarly to the small scale bioreactor, according to embodiments of the invention, the relative amounts of the secondary metabolites in pomegranate cells grown in the large scale bioreactor are not significantly reduced in comparison to their relative amounts in any of the previous steps of the process. According to some embodiments, the components described above for use in the growth medium in any of the previous steps may be used also in the third step of the process. According to some embodiments, the growth medium used in the large scale bioreactor is the same as used in any of the previous steps of the large scale process. According to some embodiments, the relative amounts of the different components found in the growth medium in the third step, is the same as in any of the previous steps of the process. According to other embodiments, the relative amounts of the different components found in the growth medium in the third step, differs from the relative amounts used in any of the previous steps of the process. According to some embodiments, additional materials are added to the growth medium in the third step of the process.

According to some embodiments, the large scale bioreactor includes an inlet through which the pomegranate cells from the second step, the medium, air and any additional materials are placed into the bioreactor. According to further embodiments, the large scale bioreactor includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the bioreactor once the atmosphere in the bioreactor reaches a pre-defined pressure. According to some embodiments, the predefined pressure is up to 8 PSI.

According to some exemplary embodiments, the pomegranate cells and the medium are continuously mixed during the third step. According to further embodiments, the pomegranate cells and the medium are mixed occasionally during the third step. According to some embodiments, the temperature during the third step is between 20 and 30° C. According to some embodiments, the pomegranate cells are grown in the third step for about two to three weeks. According to some embodiments, the pomegranate cells are grown in the third step for about three to five weeks. According to some embodiments, the pomegranate cells are grown in the third step for about 12 to 30 days.

Once the third step of the pomegranate cell growth is concluded, the pomegranate cells may be inoculated from the medium scale bioreactor typically by any appropriate means. For the fourth exemplary step of the large scale process, the harvested pomegranate cells are placed into a larger scale bioreactor. According to some embodiments, the larger scale bioreactor is a 1000 L reactor. According to further embodiments, the larger scale bioreactor is a 200-500 L reactor. According to further embodiments, the large scale bioreactor is a 500-1000 L reactor. According to further embodiments, the large scale bioreactor is a 1000-1500 L reactor. According to further embodiments, the large scale bioreactor is a 500-1100 L reactor.

The larger scale bioreactor may be prepared from any appropriate material, such as glass, metal, plastic and/or any type of polymer. According to some embodiments, the large scale bioreactor is disposable. If the large scale bioreactor is not disposable, according to some embodiments, it is cleaned and sterilized between uses by any appropriate means.

Similarly to the small scale bioreactors, according to embodiments of the invention, the relative amounts of the secondary metabolites in pomegranate cells grown in the larger scale bioreactor are not significantly reduced in comparison to their relative amounts in the previous steps of the process. According to some embodiments, the components described above for use in the growth medium in any of the previous steps may be used also in the fourth step of the process. According to some embodiments, the growth medium used in the larger scale bioreactor is the same as used in any of the previous steps. According to some embodiments, the relative amounts of the different components found in the growth medium in the fourth step, is the same as in any of the previous steps. According to other embodiments, the relative amounts of the different components found in the growth medium in the fourth step, differs from the relative amounts used in any of the previous steps. According to some embodiments, additional materials are added to the growth medium in the fourth step of the process.

According to some embodiments, the larger scale bioreactor includes an inlet through which the pomegranate cells from the third or second step, the medium and any additional materials are placed into the bioreactor. According to further embodiments, the larger scale bioreactor includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the bioreactor once the atmosphere in the bioreactor reaches a pre-defined pressure. According to some embodiments, the predefined pressure is up to 8 PSI.

According to some embodiments, here and in any other appropriate bioreactor, the bioreactor may include two or more inlets and/or outlets. Each inlet and/or outlet may be designated for the passage of a certain type of material or otherwise, various materials may pass through the same inlet/outlet. The various materials may pass through the inlet/outlet together or separately from one another. Any bioreactor related to herein may further include two or more inlets/outlets designated for the passage of at least one type of material.

According to some embodiments, the pomegranate cells and the medium are continuously mixed during the fourth step. According to further embodiments, the pomegranate cells and the medium are mixed occasionally during the fourth step. According to some embodiments, the temperature during the fourth step is between 20 to 30° C. According to some embodiments, the pomegranate cells are grown in the third or fourth step until they reached a cell biomass of 10% to 70% w/w of the entire mass of the medium.

According to some embodiments, the large scale process is terminated after the pomegranate cells are grown in the larger scale bioreactor. According to such embodiments, the pomegranate cells are grown in the larger scale bioreactor until they reach a cell biomass of 10% to 70% w/w. Once the cell biomass of 10% to 70% w/w is reached, the pomegranate cells are harvested from the large scale bioreactor by any appropriate means and are further processed. According to some embodiments, the pomegranate cells are further processed by ant appropriate type of drying, lyophilization, Freeze-Drying, fluidized bed air drying and Spray Drying. According to some embodiments, the processing of the pomegranate cells does not include the extraction of active ingredients therefrom.

According to some embodiments, the large scale process may include one step of inoculating the cells from a flask into a bioreactor, which can be in any size, and harvesting the cells. According to other embodiments, the pomegranate cells may be inoculated in a series of bioreactors wherein each of the bioreactors is typically larger than the previous bioreactor used. Any number of additional steps is performed according to the large scale process. The additional steps include possible intermediate steps in which the cells are harvested or inoculated and placed in a larger bioreactor and grown there until being harvested or inoculated and transferred to a larger bioreactor. According to further embodiments, the process includes additional steps for growing the pomegranate cells harvested from the large scale bioreactor.

In an embodiment of the invention, there is provided a pharmaceutical or nutraceutical composition or a food additive comprising the pomegranate cells manufactured in the large scale process of the invention. The pharmaceutical or nutraceutical composition or a food additive may be administered to the subject by oral administration.

As used herein, the phrase "pharmaceutical composition" refers to a preparation of pomegranate cell culture, as further described hereinabove, with or without other chemical components, such as physiologically suitable carriers and excipients.

In an embodiment of the invention, there is provided a method of treating an inflammatory disorder by administering to a subject in need a pharmaceutical or nutraceutical composition or a food additive comprising the pomegranate cell culture, wherein the culture is possibly manufactured according to the large scale process detailed herein and is possibly rich in secondary metabolites.

As used herein the term "treating" refers to the prevention of some or all of the symptoms associated with an inflammatory disease, a condition or disorder. The term "treating" also refers to alleviating the symptoms or underlying cause of an inflammatory disease, prolongation of life expectancy of patients having a disease, as well as complete recovery from a disease.

As used herein the phrase "inflammatory disorder" includes but is not limited to chronic inflammatory diseases and disorders and acute inflammatory diseases and disorders. Examples of such diseases and conditions are summarized infra.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 Ju n; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E, and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus *foliaceus*.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome, diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E, and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus *foliaceus*.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (*Nobile*-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a preferred embodiment of this aspect of the present invention, the disorder is atherosclerosis or an inflammatory disease of the mouth or gums.

Various aspects of the invention are described in greater detail in the following Examples, which represent embodiments of this invention, and are by no means to be interpreted as limiting the scope of this invention.

EXAMPLES

Example 1

Generation of Pomegranate Cell Lines (Calli) and Suspension Cultures in Erlenmeyer 1. Material and Methods Plant Material Pomegranate cell culture was initiated from pomegranate fruits (*Punica granatum* L.) of Wonderful and Akko varieties including all fruit parts (exocarp, mesocarp, lamellae, arils, seeds).

Establishment of Calli from Pomegranate Fruit Sections

Whole fruits were rinsed under running water and cut into quarters under aseptic conditions. Fruit sections were sterilized by agitation in 3% Na-hypochlorite solution for 20 minutes, followed by three washes in sterile water. Fruit sections were dried under sterile conditions and further dissected into ~0.5 cm sections under a cutting medium composed of half-strength Murashige and Skoog (MS) (Murashige et al Physiol. Plant, 15, 473-497, 1962) supplemented with 100 mg/L dithothreitol (DTT), 0.5 g/L polyvinylpirolidone (PVP), 150 mg/L L-cysteine 1.5 mg/L gallic acid and 150 mg/L ascorbic acid. Sections of various fruit tissues (red exocarp, white mesocarp, and thin white lamelles) were cultured. Arils were smashed and seeds were sterilized and rinsed as above. Seeds were cut under cutting medium and plated.

Fruit tissues and seeds were plated on MS basal medium supplemented with sucrose, casein hydrolysate, myo inositol and various combinations of the auxines 2,4-dichlorophenoxyacetic acid (2,4-D), 1-naphthaleneacetic acid (NAA) and the cytokines kinetin and benzyladenine (BA) at various concentrations. Medium pH was reached to 5.8. The medium was solidified with agar (Gelrite, Duchefa or Phytagel, Sigma). Plate compositions are specified in Table 1. Plates were kept at 25° C. in the dark or under 100 $\mu mole^{-2}$ $sec^{-1}$ irradiance, provided by cool white fluorescent lamps. When formed calli reached a diameter of 1 cm, they were split in a 1:3 ratio onto a similar medium. Calli were transferred to fresh plates every 4 weeks.

Establishment of Liquid Cultures Cell suspension cultures were initiate from calli by culturing calli fragments of about ~0.5 cm³ into a 50 ml Erlenmayer flask containing 10 ml of liquid callus inducing medium (without Gelrite) under agitation on a rotatory shaker using 100 rpm, under the same physical conditions as described for the callus cultures. Suspension culture was transferred to increasing volumes of up to ~220 ml culture in a 1 L Erlenmayer flask. Subcultures were carried out at a ~2-week interval.

TABLE 1

Media composition of various MS plates used for pomegranate calli

|  | M-1 | M-2 | M-3 | M-4 | M-5 | M-6 | M-7 | M-9 | M-10 |
|---|---|---|---|---|---|---|---|---|---|
| Kinetin (mg/L) | 0.2 | 0.2 | 0.5 |  |  | 0.1 |  |  |  |
| 2,4,D (mg/L) |  |  | 0.5 | 0.5 | 2 |  |  | 0.5 | 1 |
| NAA (mg/L) | 0.1 | 0.1 |  |  |  | 0.1 | 0.1 |  |  |
| BA(mg/L) |  |  |  |  |  | 0.3 | 2 | 0.5 | 1 |
| Casein hydrolysate (g/L) | 0.25 | 0.25 |  | 0.25 |  |  |  |  |  |
| Myo inositol (g/L) | 0.1 |  |  | 0.1 |  |  |  |  |  |
| Sucrose (g/L) | 20 | 20 | 40 | 30 | 30 | 30 | 30 | 40 | 40 |
| Agar (g/L) | 2.5 | 8 | 6 | 9 | 2.5 | 2.5 | 2.5 | 2.5 | 2.5 |

Calli Results

Culture Growth:

Forty-one calli were successfully developed from pomegranate explants (table 2). The majority of the calli (32) were developed from Akko cv. pomegranate, all of which resulted from seed explants. Nine calli were developed from Wonderful cv. pomegranate, six of which resulted from seed explants and three from mesocarp lamellae explants.

TABLE 2

The efficiency of pomegranate calli production from various pomegranate fruit sections of Wonderful and Akko cultivars

| Cultivar | Total number of calli | Calli from mesocarp-lamellae | Calli from seeds |
|---|---|---|---|
| Wonderful | 9 | 3 | 6 |
| Akko | 32 |  | 32 |
| Total | 41 | 3 | 38 |

The Effect of Media Composition:

Calli growth was detected on MS plates including various media components (M-1, M-2, M-3, M-4, M-5 M-6, M-7 M-9 and M-10 (table 1). However, as can be seen in table 3, the most callus development-promoting media compositions were the following: MS including 4% sucrose, 0.5 mg/L kinetin and 0.5 mg/L 2,4,D (M-3, eleven calli), MS including 3% sucrose, 0.1 mg/L kinetin, 0.1 mg/L NAA and 0.3 mg/L BA (M-6, seven call), MS including 3% sucrose, 0.1 mg/L NAA and 2 mg/L BA (M-7, nine calli) and MS including 3% sucrose, 0.5 mg/L 2,4,D, and 0.5 mg/L BA (M-9, four calli).

TABLE 3

The efficiency of pomegranate calli production (number of well-established calli) on various MS plates

|  |  | M-1 | M-2 | M-3 | M-4 | M-5 | M-6 | M-7 | M-9 | M-10 |
|---|---|---|---|---|---|---|---|---|---|---|
|  | Total number of calli | 2 | 1 | 11 | 4 | 2 | 7 | 9 | 4 | 1 |
| Plant part | Calli from inner mesocarp (lamellae) | 1 |  |  | 2 |  |  |  |  |  |
|  | Calli from aril (including seed) | 1 | 1 | 11 | 2 | 2 | 7 | 9 | 4 | 1 |

Establishment of Suspension Culture

Several different calli were transferred to liquid media for the generation of suspension cultures. Pomegranate suspension culture growth was efficient in liquid M-6 medium and in Gamborg B5 medium supplemented with 2-3% sucrose, 0.25 g/L casein hydrolysate and 0.1 g/L myo inositol, 0.1 mg/L NAA and 0.2 mg/L kinetin (pH 5.4-5.45), designated E-med.

The suspension cultures maintained stable growth in suspension (50 to 1000 ml Erlenmeyer flasks). Cultures were routinely subcultured every 7-20 days to fresh growth media.

Erlenmeyer, Shake Flasks

Pomegranate cells were grown in suspension under continuous fluorescent light (1000 lx) at 25+5° C., in 1 liter Erlenmeyer flasks on an orbital shaker.

Preparation of Pomegranate Cell Powder

The cultured pomegranate cells grown in liquid medium were filtered through filter and dried by lyophilization or by other drying method. Alternatively, the cultured pomegranate cells were filtered, stored at (−20° C.) and lyophilized. Alternatively, the cultured pomegranate cells were filtered, ground immediately under liquid nitrogen and lyophilized to a fine powder Example 2

Expression Polyphenolic Compounds in Pomegranate Cell Lines (Call and in Suspension Cultures in Erlenmeyer Flasks).

Materials and Methods

Polyphenols Extraction for HPLC Analysis:

Fresh and dried Pomegranate Callus cell culture were extracted for analytical determination of polyphenol content in the pomegranate culture. About 0.5 gr of callus was harvested and kept at (−20)° C. for at least 16 h before analysis. Callus was extracted by 80% methanol/water solution in a ratio of 0.4 ml methanol per 0.5 gr of cells.

Suspension was sonicated for 10 minutes at 30° C. in a sonicator. The solution was centrifuged and the supernatant was re-centrifuged, filtered through a 0.45 µm filter and used for HPLC analysis.

Pomegranate suspension cells culture samples (~10 ml) were filtered through a Buchner funnel coated with filter paper (Nr. 4, NM 617, 70 mm). Samples of 0.5 gr were kept at (−20° C.) for at least 16 h before analysis.

Cell suspension samples were extracted in 80% methanol (800 µl/0.5 gr of filtrated cells), as described above. Punicalagin α+β (punicalagins) content was monitored at 374 nm using commercial punicalagin α+β (Sigma) as a standard and expressed as µg of punicalagin per mg of fresh cell weight. Total 1,2,3,4,6-pentagalloyl glucose (PGG) content was monitored at 278 nm using commercial PGG (Sigma) as a standard, and expressed as µg of PGG per mg of fresh cells. Total polyphenols were monitored at 280 nm using commercial Epicatechin (Sigma) as a standard, and expressed as µg epicatechin equivalent.

Pomegranate tissues (red and white exocarp, white lamelles and seeds) were crushed under liquid nitrogen and extracted as described above, the extract was analyzed by HPLC and used as a reference for pomegranate polyphenols content.

HPLC Analysis

Polyphenolic compounds in a pomegranate-derived culture were characterized and quantitated by high performance liquid chromatography (HPLC) analysis. Selected phenolic compounds were identified by their UV absorbance spectra and retention times. Their concentrations were determined by means of a calibration curve using different external standards. Analysis was performed by JASCO PU-2089 HPLC system using the operation software ChromNAV. Total polyphenols were determined by summing AUC of peaks as monitored at 280 nm, and quantified, based on epicatechin as a standard. Total polyphenols is expressed as epicatechin equivalents. Punicalagin was monitored at 254 and 374 nm, based on characteristic absorption, and quantified according to a commercial punicalagin standard curve. PGG was monitored at 278 nm, based on characteristic absorption, and quantified according to a commercial PGG standard curve.

Liquid Chromatography Mass Spectrometry (LC-MS) Analysis

LC-MS analysis of the sample was performed using an Accela LC system coupled with an LTQ Orbitrap Discovery hybrid FT mass spectrometer (Thermo Fisher Scientific Inc.) equipped with electrospray ionization source. The mass spectrometer was operated in negative ionization mode, wherein ion source parameters were as follows: spray voltage 3.5 kV, capillary temperature 300° C., ion-transfer optics parameters were optimized using automatic tune option, sheath gas rate (arb) 35, and auxiliary gas rate (arb) 15.

Mass spectra were acquired in the m/z 150-2000 Da range. The LC-MS analysis was performed in data depending acquisition mode. The LC-MS system was controlled and the data were analyzed using Xcalibur software (Thermo Fisher Scientific Inc). Chromatographic separation was achieved on Kinetex Hexyl-Phenyl column (2.6 mm, 150×2.1 mm, Phenomenex) using an ACN/Water+0.1% AcOH (in both) gradient.

Results

Polyphenolic Compound Expression

Expression of various polyphenolic compounds that are produced in pomegranate fruit was also detected in fresh and dried pomegranate calli and in suspension cultures. These compounds include flavonoids, phenolic acids and tannins. Amongst these compounds, significant amounts of punicalagins, punicalins, gallic and ellagic acids and large amounts of 1,2,3,4,6-pentagalloyl glucose (PGG) were detected, as confirmed by LC-MS. Expression of punicalagins and PGG in addition to other polyphenolic compounds, was detected in some of the developed calli (Table 4)

TABLE 4

Amounts of punicalagin and PGG in calli growing on various MS plates

| | | M-1 | M-2 | M-3 | M-4 | M-5 | M-6 | M-7 | M-9 | M-10 |
|---|---|---|---|---|---|---|---|---|---|---|
| Range (µg/mg fresh weight) | Punicalagin | ND | ND | ND | 0.01-0.14 | ND | 0.03-0.1 | 0.18 | 0.15 | ND |
| | PGG | ND | ND | 0.2-0.26 | 0.1-0.17 | ND | 0.08-0.1 | 0.25 | 0.1-0.25 | ND |

Total Polyphenols PGG and Punicalagin Quantitation in Pomegranate Suspension Culture Punicalagins content in various pomegranate calli grown on various MS plates ranged from 0-0.18 µg/mg of fresh weight (n=43). Punicalagins content in various pomegranate cell suspension cultures derived from callus and grown in flasks in E-med ranged from 0.1-0.7 µg/mg of fresh weight (n=7). PGG content in pomegranate calli ranged from 0-0.26 µg/mg of fresh weight (n=43). PGG content in pomegranate cell suspension cultures grown in flasks ranged from 0.2-1.1 µg/mg of fresh weight (n=7). Considering an average drying factor of 20, punicalagin content in suspension culture in flasks is equivalent to 2-14 µg/mg dry weight (0.2-1.4%). Similarly, PGG content in suspension culture in flask is equivalent to 4-22 µg/mg dry weight (0.4-2.2%). Total polyphenols, punicalagins and PGG content in different parts of pomegranate fruit as compared to pomegranate suspension cultures is summarized in Table 5.

Form the various medium that were used, E-med was found to be the best medium for growing pomegranate cell cultures having large amounts of total polyphenols, punicalagins and PGG in a suspension.

TABLE 5

Total polyphenols, PGG (1,2,3,4,6-pentagalloyl glucose) and Punicalagin content in pomegranate fruit parts from prior art documents compared to the pomegranate cells (PGC) grown in vitro of the invention

| Source | Pom. variety | Punicalagin | Total polyphenols | PGG (1,2,3,4,6-pentagalloyl glucose) | Ref |
|---|---|---|---|---|---|
| Pomegranate white Mesocarp and red peel | 3 un-known varieties | 1.1-2.0% (DW) | 4.4 and 4.0% (DW) | Not reported | 1 |
| Pomegranate Juice | | 0.0004-0.0565% | 0.013-0.21% | | |
| Pomegranate Peel | | 8.24% DW | | Not reported | 2 |
| Commercial juices | Mollar | 0.05-0.076% | 0.11-0.36% | Not reported | 3 |
| Pomegranate juices | | 0.0002-0.0041% | 0.008-0.013% | Not reported | 4 |
| Fruitura Pomegranate cells (PGC) in calli (solid media) | Dry weight | 0-0.6% | 0-22% | 0-0.6% | |
| Fruitura Pomegranate cells (PC) in flask suspension culture (Erlenmeyer) | dry weight | 0.2-1.4% dry weight | 7-30% in dry weight | 0.4-2.2% dry weight | |
| Fruitura Pomegranate cells (PC) in bioreactors (small scale, large scale and larger scale) suspension culture | dry weight | 0.8-1.8% in dry weight | 10-70% in dry weight | 0.4-3.2% in dry weight | |

Note:
total polyphenols, punicalagin and PGG in pomegranate parts and juice were taken from the references below:
1. Fischer, U. A., Carle, R. & Kammerer, D. R. Identification and quantification of phenolic compounds from pomegranate (Punica granatum L.) peel, mesocarp, aril and differently produced juices by HPLC-DAD-ESI/MS(n). *Food chemistry* 127, 807-821 (2011).
2. Lu Jingjing, D. K. Y. Q. Determination of Punicalagin Isomers in Pomegranate Husk. *Chromatographia* 68 303-306 (2008).
3. Vegara, S., et al. Chemical guide parameters for Punica granatum cv. 'Mollar' fruit juices processed at industrial scale. *Food chemistry* 147, 203-208 (2014).
4. Herrera-Hernandez, M. G. M. J., Candelario Soria-Lara, Dulce M. and Guzman MaldonadoSalvador H. Comparative study of Physicochemical and Functional Characteristics in Juices from New Mexican Pomegranate Cultivars (PunicagranatumL.) and Wonderful Variety. *Biochemistry and Biophysics (BAB) Volume 1 Issue 3, September 2013* 1, 35-42 (2013).

Example 3

Scale Up of Pomegranate Culture in Bioreactors of Up to 1000 L and Testing of Total Polyphenols, Punicalagins and PGG Content in Pomegranate Cells Grown in Large Scale Bioreactor Materials and Methods Stage 1: cells are prepared and grows as described in example 1.

Stage 2: Small scale bioreactor

Small scale bioreactor culturing is performed by inoculating a 7 to 16 old day cell suspensions grown in the Erlenmeyer of Stage 1 into a 4-8 liter disposable bioreactor at 25+5° C. The cells are grown in the suspension under continuous fluorescent light (1000 lx) in a growing medium containing enriched Gamborg B5 salt and vitamins medium supplemented with 250 mg/l casein hydrolizate, 2-4% sucrose and 100 mg/l Myo-inositol (pH 5.4-5.8). The cells are sub-cultured every 9-21 days.

Stage 3: Large scale bioreactor

The cell suspension grown in a small scale bioreactor are inoculated into a 30-50 liter disposable bioreactor. The cells are grown in a suspension under continuous fluorescent light (1000 lx) at 25+5° C. The growing medium containing enriched Gamborg B5 salt and vitamins medium supplemented with 250 mg/l casein hydrolisate, 2-4% sucrose, 100 mg/l Myo-inositol, 25-45 mM KNO3, 1-15 mM MgSO4 or 5-35 mM MgNO3 and 1 mM NaH2PO4, 0.2 mg/l Kinetin and 0.1 mg/l NAA (1-naphthaleneacetic acid) (pH 5.4-5.8). The cells are sub-cultured every 12-30 days.

Stage 4: Larger scale bioreactor

The cell suspension grown in a small or large scale bioreactor are inoculated into a 300-1000 liter disposable bioreactor. The cells are grown in a suspension under continuous fluorescent light (1000 lx) at 25+5° C. The growing medium contains enriched Gamborg B5 salt and vitamins medium supplemented with 250 mg/l casein hydrolisate, 2-4% sucrose, 100 mg/l Myo-inositol, 25-45 mM KNO3, 1-15 mM MgSO4 or 5-35 mM MgNO3 and 1 mM NaH2PO4, 0.2 mg/l Kinetin and 0.1 mg/l NAA (1-naphthaleneacetic acid) (medium pH 5.4-5.8).

Stage 5: Harvesting

The cells are harvested once they reach a cell biomass of 10% to 70% (w\v). The harvested cells are dried (for example in a spray dryer) to produce a fine green powder, with a typical composition, taste and odor.

The content of punicalagin and PGG in small, large and larger scale bioreactors of pomegranate cell suspension cultures was determined by HPLC, as described in example 2. Punicalagins content in bioreactors (comprising: small scale, large scale and larger scale) ranged from 0.4-0.9 µg/mg of fresh weight (n=16). PGG content in bioreactors (comprising: small scale, large scale and larger scale) ranged from 0.2-1.6 µg/mg of fresh weight (n=10). Considering an average drying factor of 20, punicalagin content in suspension culture in flasks is equivalent to 8-18 µg/mg dry weight (0.8-1.8%). Similarly, PGG content in bioreactors it is equivalent to 4-32 µg/mg dry weight (0.4-3.2%). Punicalagins and PGG content in pomegranate suspension cultures is summarized in Table 5

As can be clearly seen from Table 5 the concentration of punicalagin and PGG in cultures is elevated during the scale up process i.e. from callus culture to suspension culture, and is further increased with the up-scaling of bioreactor size. The growth of suspension cultures in bioreactors induced the cells to produce ~1.3 fold and 1.5 folds of punicalagin and PGG, respectively as compared to the concentration of those ingredients in flask-size cultures, and ~3 fold and ~5 folds of punicalagin and PGG, respectively as compared to callus cultures. This indicates that the scale up process suggested herein in which bioreactors and specific medium are used is required for the production in vitro pomegranate cell cultures having high amount of punicalagin and PGG.

Example 4

The Effect of Medium Composition and Bioreactor Design on the Level of Total Polyphenols, Punicalagins and PGG Content in Pomegranate Cells Grown in Large Scale Bioreactor The content of punicalagin and PGG in pomegranate cell suspension cultures in various medium compositions was determined by HPLC, as described in example 2.

The content of punicalagin and PGG in small, large and larger scale bioreactors of pomegranate cell suspension cultures was determined by HPLC, as described in example 2. Punicalagins content in bioreactors (comprising: small scale, large scale and larger scale) ranged from 0.4-0.9 µg/mg of fresh weight (n=16). PGG content in bioreactors (comprising: small scale, large scale and larger scale) ranged from 0.2-1.6 µg/mg of fresh weight (n=10). Considering an average drying factor of 20, punicalagin content in suspension culture in flasks is equivalent to 8-18 µg/mg dry weight (0.8-1.8%). Similarly, PGG content in bioreactors it is equivalent to 4-32 µg/mg dry weight (0.4-3.2%). Punicalagins and PGG content in pomegranate suspension cultures is summarized in Table 5

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention

The invention claimed is:

1. A scale-up process for the in vitro production of a pomegranate fruit cell culture of pomegranate aril cells grown comprising:
    growing pomegranate aril cells in a flask;
    inoculating the pomegranate aril cells from the flask into a first bioreactor;
    inoculating the pomegranate aril cells from the first bioreactor into a second bioreactor; and
    harvesting the pomegranate aril cells from the last bioreactor;
    wherein the second bioreactor is a last bioreactor or an intermediate bioreactor;
    wherein at least one of the first and the second bioreactor is disposable;
    wherein the pomegranate aril cells harvested from the last bioreactor are dried;
    wherein the size of each bioreactor used in the process is larger than the one in which the pomegranate aril cells were previously grown;
    wherein the pomegranate aril cells harvested from the last bioreactor comprise a total polyphenol concentration of between 100,000-700,000 mg/kg dry weight powder;
    wherein the pomegranate aril cells are grown in a growth medium comprising Gamborg B5 medium at pH of 5.4-5.8 comprising 2-4% sucrose, 0.2-0.3 g/L casein hydrolysate, 0.05-0.15 g/L myo inositol, 0.05-0.15 mg/L 1-naphthaleneacetic acid (NAA) and, 0.1-0.3 mg/L kinetin, 25-45 mM KNOB, 1-15 mM $MgSO_4$ or 5-35 mM $MgNO_3$ and 1 mM $NaH_2PO_4$.

2. The process of claim 1, wherein if the second bioreactor is an intermediate bioreactor, an additional step of inoculating the pomegranate aril cells to another bioreactor is performed.

3. The process of claim 1, wherein any one of the bioreactor is a 4-10 liter bioreactor.

4. The process of claim 1, wherein any one of the bioreactor is a 10-50 liter bioreactor.

5. The process of claim 1, wherein any one of the bioreactor is a 50-200 liter bioreactor.

6. The process of claim 1, wherein any one of the bioreactor is a 200-500 liter bioreactor.

7. The process of claim 1, any one of the bioreactor is a 200-1000 liter bioreactor.

8. The process of claim 1, wherein the disposable bioreactor is made from one or more layers of polyethylene.

9. The process of claim 8, wherein the disposable bioreactor is made from an inner and outer layer of polyethylene and a middle nylon layer.

10. The process of claim 1, wherein the growth medium includes plant hormones.

11. A composition in a form of a powder produced by the method of claim 1 and having a total polyphenol concentration of between 100,000-700,000 mg/kg dry weight powder.

12. The composition according to claim 11, wherein the pomegranate aril cells include a complex of polyphenols, punicalagin, 1,2,3,4,6-pentagalloyl glucose (PGG) or a combination thereof.

13. A method of treating inflammation comprising:
    administering an effective amount of the composition of claim 11 to a subject in need.

* * * * *